United States Patent [19]

Fawcett et al.

[11] Patent Number: 4,742,175

[45] Date of Patent: May 3, 1988

[54] PREPARATION OF POLYMORPHICALLY PURE TERFENADINE

[75] Inventors: Timothy G. Fawcett; Christian T. Goralski; David W. Ziettlow, all of Midland, Mich.

[73] Assignee: Merrell Dow Pharmaceuticals Inc., Cincinnati, Ohio

[21] Appl. No.: 68,752

[22] Filed: Jun. 30, 1987

Related U.S. Application Data

[63] Continuation of Ser. No. 860,619, May 7, 1986, abandoned.

[51] Int. Cl.$^4$ ............................................. C07D 211/22
[52] U.S. Cl. ................................................... 546/241
[58] Field of Search ......................................... 546/241

[56] References Cited

U.S. PATENT DOCUMENTS 3,878,217  4/1975  Carr et al. .......................... 546/191

Primary Examiner—Norma S. Milestone
Attorney, Agent, or Firm—Stephen L. Nesbitt

[57] ABSTRACT

Polymorphically pure terfenadine, 1-(p-tert-butylphenyl)-4-[4'-(α-hydroxydiphenylmethyl)-1'-piperidinyl]-butanol, is prepared by carefully controlled recrystallization methods.

11 Claims, No Drawings

PREPARATION OF POLYMORPHICALLY PURE TERFENADINE

CROSS REFERENCE TO RELATED APPLICATION

This is a continuation of application Ser. No. 860,619, filed May 7, 1986, now abandoned.

BACKGROUND OF THE INVENTION

Terfenadine, 1-(p-tert-butylphenyl)-4-[4'-(α-hydroxydiphenylmethyl)-1'-piperidinyl]butanol, is a non-sedating antihistamine. Previous crystallization procedures for terfenadine produce a product which, although analytically pure, nevertheless has widely variable melting point. Recently, it was discovered that solid terfenadine exists in two distinct crystalline or polymorphic forms, each form having a different melting point. It was further discovered that terfenadine crystallized by the prior art processes varies widely in polymorphic composition and that this polymorphic variation accounted for the observed variation of the melting point of terfenadine. Applicants have now discovered processes for preparing polymorphically pure terfenadine. These processes provide material with a controlled set for physical properties which should facilitate quanlity control functions associated with large scale production of terfenadine.

The higher melting polymorph of terfenadine is prepared by dissolving terfenadine in a water-miscible, lower alkanol, heating the solution at about its reflux temperature, slowly adding a sufficient quantity of water with stirring to effect crystal formation of substantially all of the dissolved terfenadine, cooling to about 25° C. and collecting the crystalline product. The lower melting polymorph of terfenadine is prepared by dissolving terfenadine in a suitable solvent at about 0° C. to about 35° C., allowing the solvent to slowly evaporate and collecting the resulting crystalline product.

DETAILED DESCRIPTION OF THE INVENTION

The higher melting polymorph of terfenadine is that substantially pure crystalline form of terfenadine having a melting point of about 149°–151° C. The lower melting polymorph of terfenadine is that substantially pure crystalline form of terfenadine having a melting point of 146° C.

The term "lower alkanol solvent" means any water-miscible, lower alkanol in which terfenadine is soluble and includes those primary, secondary and tertiary alcohols of from 1 to 6 carbon atoms. Suitable lower alkanol solvents include methanol, ethanol, n-propanol, isopropanol, isobutanol, amyl alcohol, t-butanol and cyclohexanol. Preferably, the lower alkanol solvent used in the preparation of the higher melting polymorph of terfenadine will be methanol, ethanol or propanol. Ethanol is the most preferred solvent. Mixtures of two or more lower alkanols is also contemplated as well as solutions of water with a lower alkanol, wherein the water will comprise up to about 10% to 20% of the solution by weight.

The solutions of terfenadine in the lower alkanol solvent are prepared conventionally. Typically, solutions of a substance to be recrystallized will be highly concentrated, near the saturation point of solute in solvent. For example, where ethanol is the solvent, the weight to volume ratio of terfenadine to ethanol can be from 0.1 g/ml to 0.3 g/ml, preferably from 0.15 g/ml to 0.25 g/ml. Typically, solutions to be recrystallized are heated and generally the temperature of the solution to be recrystallized will be at about the reflux temperature of the solution. Where ethanol is the solvent this temperature will be about 78° C. It is preferable to filter the hot, concentrated solution prior to crystal formation in order to remove any insoluble, particulate material. Filtration is especially important where the higher melting polymorph of terfenadine is to be prepared directly from impure terfenadine.

Water is added to the heated, concentrated solutions in order to cause crystallization of terfenadine. Preferably a sufficient quantity of water will be added so that substantially all of the terfenadine will crystallize. Where ethanol is the solvent, the volume to volume ratio of ethanol to water can be from 0.75 to 1.5 ml/ml, preferably about 1 ml/ml. Preferably less than ten percent of the dissolved terfenadine will remain in solution after complete addition of the water. The quantity of water required will depend on a variety of factors including the solvent, the temperature of the heated, concentrated solution and the concentration of the solution. The quantity of water required to receiver substantially all of the terfenadine as crystals of the high melting polymorph can be readily determined by any skilled artisan.

The water to be added to the heated, concentrated terfenadine solution is preferably also heated, preferably to a temperature of from 60° C. to 100° C. Preheating of the water renders maintaining a constant temperature of the heated, concentrated terfenadine solution easier.

It is preferable that the water be added to the heated, concentrated terfenadine solution at such a rate that the temperature of the solution can be maintained at about its reflux temperature. Slow, dropwise addition with agitation, for example, agitation by stirring, is preferred. Typically, addition of the water will require from 10 minutes to 2 hours. After all the water has been added to the lower alkanol solution of terfenadine it is preferable to allow the crystals to digest prior to filtration to collect the product. Crystal digestion can be accomplished by continuing to heat the lower alkanol solution of terfenadine after the water addition is complete. Preferably the temperature during digestion will be the reflux temperature of the solution but can be any temperature about ambient temperature. Digestion can proceed for any amount of time up to about a day, preferably for about 0 to 6 hours.

After complete addition of the water to the heated, concentrated solution of terfenadine in lower alkanol and after crystal digestion, if desired, the resulting mixture is allowed to cool to ambient temperature, about 25° C. Preferably this cooling is accomplished by simply removing the heat source and is not accelerated by any cooling means. Once cooled to ambient temperature, the mixture is then cooled to about 0°–5° C. by the use of, for example, a simple ice-water bath. Salts such as sodium chloride or calcium chloride can be used to lower the temperature of the cooling bath to even lower temperatures, if desired. The cooled mixture is then filtered from the slurry to collect the solid product. The solid product can be washed with additional water, preferably small amounts of cold water or mixtures of water and alkanol such as 50% aqueous ethanol. The product is then dried by conventional means such as under vacuum and can be heated to promote loss of residual water and lower alkanol, preferably to about 50°–75° C., most preferably to about 60° C.

The term "suitable solvent" when used herein in relation to the preparation of the lower melting polymorph of terferadine means any solvent in which terfenadine is soluble, such as a hydrocarbon solvent, that is a solvent containing only the elements of carbon and hydrogen such as pentane, hexane, benzene, toluene and xylene or a ketone or aldehyde, having from 1 to 10 carbon atoms, such as methyl ethyl ketone, 2-butanone, cyclopentanone, isopropylmethyl ketone and acetophenone can also be used. Mixture of two or more lower ketones is also contemplated. Ketone solvents are preferred as well as toluene. Acetone is the most preferred solvent.

The solutions of terfenadine are prepared conventionally by simply adding the solvent with a polymorphic mixture of terfenadine or to the higher melting polymorph of terfenadine, with stirring. Substantially pure terfenadine, that is terfenadine substantially free of contaminants other than the polymorphs of terfenadine, should be used when preparing solutions for the purpose of preparing the pure, lower-melting polymorph of terfenadine.

Heating to increase the rate of dissolution is not preferred and unlike solutions to be used to recyrstallize the solute, the solution of terfenadine in lower ketone solvents used herein need not be saturated or substantially near saturation. A solution of 50 mg of terfenadine in about 12 ml of acetone, for example, is satisfactory. Filtration of the solution to remove any undissolved terfenadine or other impurity is preferred.

The lower-ketone solvent is then allowed to evaporate. Slow evaporation is preferred, such as, by allowing the solution to stand in an open container at room temperature for from several hours to several days. For example, a solution of 50 mg of terfenadine in 12 ml of acetone was allowed to evaporate over a 2-day period. Heating to increase the rate of evaporation is not preferred. Room temperature evaporation is preferred. The use of a vacuum system is also not preferred but good air circulation to prevent undue built up of evaporated solvent is encouraged. The resulting crystalline product is the substantially pure, lower melting polymorph of terfenadine.

EXAMPLE 1

PREPARATION OF THE LOWER-MELTING POLYMORPH OF TERFENADINE FROM ACETONE SOLUTION

Approximately 50 mg of terfenadine (19% higher-melting polymorph, 81% lower-melting polymorph) was dissolved in 12 ml of acetone at room temperature. The acetone was then slowly evaporated over a 2-day period. The dried product, terfenadine, was 100% lower-melting polymorph.

EXAMPLE 2

PREPARATION OF THE HIGHER-MELTING POLYMORPH OF TERFENADINE

A 500 ml Erlenmeyer flask equipped with a magnetic stirrer was charged with 72.6 g of wet and impure terfenadine (ca 51% water). The flask was then charged with 250 ml of absolute ethanol and the slurry heated to reflux to form a cloudy solution. The solution was filtered hot into a one-liter, three-neck flask equipped with a mechanical stirrer, a reflux condenser fitted with a nitrogen bubbler, and a pressure-equalizing addition funnel. The ethanol solution was held at reflux, and 200 ml of deionized water was slowly added over 30 minutes causing crystallization of the terfenadine. The resulting slurry was then heated at reflux for 5 hours to crystal digest the product. The slurry was then cooled slowly to room temperature. The slurry was then cooled in an ice-bath for 30 minutes. The solid was filtered from the slurry, washed with 50 ml of 50/50 (v/v) ethanol/water, washed with two 50-ml portions of water, air dried, and vacuum dried at 60° C. to give 37.0 of terfenadine as pure higher-melting polymorph. m.p. 149.5°–151° C.

Anal.: Calc'd for $C_{32}H_{41}NO_2$: C, 81.48; H 8.76; N, 2.97. Found: C, 81.5; H, 8.70; N, 2.94. Residue on ignition: 0.02%.

EXAMPLE 3

PREPARATION OF TERFENADINE

A one-liter, three-neck flask equipped with a mechanical stirrer, a pressure-equalizing addition funnel and a reflux condenser fitted with nitrogen bubbler was charged with 72.8 g (0.149 mol) of terfenadone monohydrate and 320 ml of absolute ethanol. The mixture was heated to reflux, a clear solution formed and a solution of 12.0 g (0.317 mol) of sodium borohydride in 83.2 g of 50% sodium hydroxide and 25.6 ml of water was added dropwise, with stirring, over a period of 1 hour. After the addition was complete, the reaction mixture was stirred at reflux for 2 hours. Terfenadine begain to crystallize. The slurry was then diluted with 320 ml of water by adding the water at such a rate that the reaction remained at reflux. The slurry was then cooled slowly to room temperature. The solid was filtered from the slurry, washed with 100 ml of 50/50 (v/v) ethanol/water, washed with two 250-ml portions of deionzied water, air dried, and vacuum dried at 60° C. to give 68.2 g (97% yield) of terfenadine as a mixture of polymorphs, m.p. 149.5°–150° C.

EXAMPLE 4

PREPARATION OF THE HIGHER-MELTING POLYMORPH OF TERFENADINE

The terfenadine obtained from Example 3 was charged to a one-liter Erlenmeyer flask and mixed with 250 ml of absolute ethanol. The mixture was heated to reflux to give a cloudy, colorless solution. The solution was filtered into a one-liter, three-neck flask equipped with a mechanical stirrer, a pressure-equalizing addition funnel, and a reflux condenser fitted with a nitrogen bubbler. The flask and the filter was washed with 70 ml of refluxing ethanol. The filtrate was held at reflux and 320 ml of deionized water were added at such a rate that the mixture remained at reflux. After the addition was complete, the resulting slurry was held at reflux for 10 minutes and then cooled slowly to room temperature. The solid was filtered from the slurry, washed with 100 ml of 50/50 (v/v) ethanol/water, washed with two 250-ml portions of deionized water, air dried, and vacuum dried at 60° C. to give 66.2 g (97% recovery) of terfenadine, m.p. 148.5°–150° C. This represents a 94% yield of terfenadine from terfenadone through the reduction, crystallization and recrystallization.

Anal.: Calc'd for $C_{32}H_{41}NO_2$: C, 81.48; H, 8.76; N, 2.97. Found: C, 81.7; H, 8.89; N, 2,87. Residue on ignition: not detected at a limit of 0.04%.

EXAMPLE 5

PREPARATION OF THE LOWER-MELTING POLYMORPH OF TERFENADINE FROM TOLUENE SOLUTION

Approximately 50 mg of terfenadine (19% higher-melting polymorph, 81% lower-melting polymorph) was dissolved in 12 ml of toluene at room temperature. The toluene was then slowly evaporated over a 2-day period. The dry product was 100% pure lower-melting polymorph of terfenadine.

What is claimed is:

1. A process for preparing the higher-melting polymorph of terfenadine which comprises dissolving terfenadine in a water-miscible, lower alkanol, heating the solution at about its reflux temperature, slowly adding a sufficient quantity of water with stirring to effect substantial crystallization of terfenadine, cooling, and collecting the crystalline product.

2. A process according to claim 1 wherein the water-miscible, lower alkanol is methanol, ethanol or isopropanol.

3. A process according to claim 1 wherein the water-miscible, lower alkanol is ethanol.

4. A process according to claim 1 wherein the weight to volume ratio of terfenadine to ethanol in the solution is from 0.1 g/ml to 0.3 g/ml.

5. A process according to claim 3 wherein the volume to volume ratio of ethanol to water is about 0.75 ml/ml to 1.5 ml/ml.

6. A process according to claim 3 wherein the volume to volume ratio of ethanol to water is about 1.0 ml/ml.

7. A process according to claim 3 wherein the temperature of the solution of terfenadine in ethanol is about 78° C.

8. A process according to claim 1 wherein a solution of terfenadine in ethanol, having a weight to volume ratio of terfenadine to ethanol of about 0.15 to 0.25 is heated to 78° C., sufficient water to result in a volume to volume ratio of ethanol to water of about 1 ml/ml was added over about 30 minutes, the resulting slurry was heated at its reflux temperature for from 0 to 5 hours, cooled slowly to room temperature, then cooled to from 0° C. to 5° C., filtered and the recovered terfenadine dried.

9. A process for preparing the lower-melting polymorph of terfenadine which comprises dissolving terfenadine in a suitable solvent at about 0° C. to about 35° C., allowing the solvent to slowly evaporate and collecting the crystalline product.

10. A process according to claim 9 wherein the solvent is acetone.

11. A process according to claim 9 wherein the solvent is toluene.

* * * * *